United States Patent [19]

Mendenhall

[11] Patent Number: 4,460,513

[45] Date of Patent: Jul. 17, 1984

[54] METHOD FOR PREPARING ORGANIC HYPONITRITES

[75] Inventor: G. David Mendenhall, Hancock, Mich.

[73] Assignee: Board of Control of Michigan Technological University, Houghton, Mich.

[21] Appl. No.: 436,634

[22] Filed: Oct. 25, 1982

[51] Int. Cl.$^3$ .................... C07C 77/00; C07C 77/02
[52] U.S. Cl. .................................... 260/466; 260/467
[58] Field of Search ............... 260/466, 467, 453 R; 526/209, 219

[56] References Cited

U.S. PATENT DOCUMENTS

| | | | |
|---|---|---|---|
| 2,946,776 | 7/1960 | Blackley et al. | 526/219 |
| 2,951,834 | 9/1960 | Scott | 526/219 |
| 2,961,460 | 11/1960 | Scott | 260/453 R |
| 3,042,663 | 7/1962 | Scott | 526/209 |
| 3,044,997 | 7/1962 | Seed | 260/466 |

FOREIGN PATENT DOCUMENTS

| | | |
|---|---|---|
| 618168 | 4/1949 | United Kingdom . |
| 813460 | 5/1959 | United Kingdom . |
| 814668 | 6/1959 | United Kingdom . |
| 831837 | 4/1960 | United Kingdom . |
| 837486 | 6/1960 | United Kingdom . |
| 848492 | 9/1960 | United Kingdom . |
| 1149451 | 4/1969 | United Kingdom . |

*Primary Examiner*—Benjamin R. Padgett
*Assistant Examiner*—T. J. Wallen

[57] ABSTRACT

Tertiary organic hyponitrite usable as initiators for polymerizing ethylenically unsaturated compounds are prepared by reacting an alkali metal, alkaline earth, ammonium or substituted ammonium salt of hyponitrite, such as sodium hyponitrite, with a tertiary organic halide, such as tert-butyl chloride, in the presence of one or more weak Friedel-Crafts catalysts, such as ferric or zinc chloride, and in a solution of a neutral solvent.

14 Claims, No Drawings

METHOD FOR PREPARING ORGANIC HYPONITRITES

BACKGROUND OF THE INVENTION

This invention relates to methods for preparing organic hyponitrites.

Organic hyponitrites, particularly alkyl hyponitrites, have been used as free-radical initiators in the polymerization of ethylenically unsaturated compounds, such as ethylene, tetrafluoroethylene, styrene and vinyl acetate, acrylate esters and other polymerizable olefins and di-olefins. The faster rate of decomposition of organic hyponitrites usually permits either lower process operating temperatures, shortened reaction times, or use of smaller molar quantities of the initiator in commercial polymerization processes.

Such organic hyponitrites typically have been synthesized from a metal hyponitrite, most commonly silver hyponitrite, and an alkyl halide. While silver hyponitrite is reactive with a broad range organic halides, the cost of silver renders this approach economically unattractive unless steps are taken to recover this silver.

Processes using metal hyponitrites other than silver hyponitrite, such as sodium hyponitrite, have been proposed. However, those processes require the use of extremely reactive halides such as α-halogenated ethers or acylating agents. α-Haloethers can be reacted with a wider variety of metal hyponitrites, but are undesirable because most of the common ones are lachrymators (induce tears), irritants, and rather potent carcinogens.

Representative prior methods for preparing organic hyponitrites useful as polymerization initiators are disclosed in U.S. Pat. Nos. 2,946,776, 2,951,834, 2,961,460 and 3,042,663 and British Pat. Nos. 618,168 (published Feb. 17, 1949), 813,460 (published May 13, 1959), 814,668 (published June 10, 1959), 831,837 (published Apr. 16, 1960), 837,486 (published June 15, 1960), 848,492 (published Sept. 21, 1960) and 1,149,451 (published Apr. 23, 1969).

Primary and secondary alkyl hyponitrites can be prepared from sodium hyponitrite and more stable α-haloethers. However, these two class of hyponitrites are inherently less efficient sources of free radicals for initiation than tertiary organic hyponitrites because of disproportionation reactions within the solvent cage which reduce the number of free radicals available for polymerization. Also, primary and secondary alkyl hyponitrites tend to decompose in the pure state and, therefore, are more difficult to store than tertiary alkyl hyponitrites.

Tertiary α-haloethers, from which the more efficient tertiary hyponitrites can be synthesized, are inconvenient intermediates because they are unstable at room temperature.

SUMMARY OF THE INVENTION

A primary object of the invention is to provide an inexpensive method for preparing organic hyponitrites.

Another object of the invention is to provide a method for preparing tertiary organic hyponitrites without the use of silver hyponitrite.

A further object of the invention is to provide a method for preparing tertiary organic hyponitrites at relatively high yields without the use of silver hyponitrites or highly reactive alkylating or acylating agents.

Other objects, aspects and advantages of the invention will become apparent to those skilled in the art upon reviewing the following detailed description and the appended claims.

According to the invention, tertiary organic hyponitrites are prepared by reacting an alkali metal, alkaline earth, ammonium or substituted ammonium salt of hyponitrite with a tertiary organic halide in the presence of a catalytic amount of one or more weak Friedel-Crafts catalysts which do not readily react with water and in a solution of a substantially neutral solvent capable of dissolving the catalyst without substantially inhibiting its catalytic activity, while maintaining the reaction medium at a temperature below the decomposition temperature of the tertiary organic hyponitrite being produced.

DESCRIPTION OF THE PREFERRED EMBODIMENTS

Alkali metal, alkaline earth, ammonium or substituted ammonium salts of hyponitrites used as one of the starting materials preferably is in a finely comminuted form.

Suitable hyponitrite salts include sodium hyponitrite, potassium hyponitrite, lithium hyponitrite, cesium hyponitrite, calciumm hyponitrite, barium hyponitrite, ammonium hyponitrite, strontium hyponitrite, magnesium hyponitrite, and tetraalkyl ammonium hyponitrites, such as tetra-n-butyl ammonium hyponitrite. At present, sodium hyponitrite is preferred because of its lower cost. Hyponitrites of some metals less expensive than silver hyponitrites, such as cupric hyponitrite, will react with tertiary organic halides, but do not produce the corresponding tertiary organic hyponitrite.

The hyponitrite salt preferably is anhydrous, in which case it usually must be treated to remove any residual water of association prior to being added to a solution or mixture containing the tertiary organic halide and the catalyst.

The tertiary organic halides have the general formula

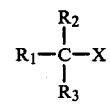

wherein $R_1$, $R_2$ and $R_3$ are aliphatic, substituted aliphatic or substituted aromatic groups and the bond between C and each $R_1$, $R_2$ and $R_3$ is connected to a saturated carbon and X is a halide.

The $R_1$, $R_2$ and $R_3$ groups can include vinyl and phenyl radicals and various other substitutes as long as they are remote from the carbon atom connected to C in the above formula. For example, benzyl halides with a phenyl group on the carbon connected to C in the atom formula, such a benzyl chloride and cumyl (α,α-dimethylbenzyl) chloride, have been found to be unsatisfactory when reacted with sodium hyponitrite and a Lewis acid catalyst even though they normally are more reactive. The $R_1$, $R_2$ and $R_3$ groups can be the same or different and preferably are saturated alkyl groups. The preferred halides are bromide and chloride.

Suitable tertiary organic halides include tert-butyl bromide, tert-butyl chloride, tert-amyl bromide, 1-methylcyclohexyl chloride, 2-bromo-2-methyloctane, 2-methyl-2-bromo-5-phenylpentane, tert-octylchloride, 2-bromo-2-methyl-5-octene, 2-ethyl-2-chloro-6-methoxyhexane and mixtures thereof.

Primary and secondary halides, such as cyclohexyl bromide, generally do not produce satisfactory results.

The amount of the tertiary organic halides used is not particularly critical. Generally, an amount equal to at least two equivalents relative to the hyponitrite salt provides a more efficient reaction. The tertiary organic halide can be conveniently recovered from the reaction product, such as by distillation or the like, so as excess can be used if desired.

The presence of one or more weak Friedel-Crafts catalysts which does not readily react with water in the reaction mixture is critical to obtaining the desired tertiary organic hyponitrite. Some of the hyponitrite salts will react with tertiary organic halides, but do not produce the desired product without such a catalyst. The function of the catalyst is not completely understood at this time and may not be strictly catalytic in all cases. Its function appears to depend on a combination of factors. One of these factors appears to be the ability to solubilize the hyponitrite ion and another factor appears to be the ability to form a significant amount of reactive alkylating species or intermediate. For example, when sodium hyponitrite is reacted with a tertiary alkyl halide in the presence of zinc chloride, it is postulated that a reactive alkylating species, such as $R^+ZnCl_3^-$, or an intermediate, such as $R^+[ZnCl_2O-N=N-Q]^-$ wherein Q is ONa, OR or OZnCl and R is an alkyl group, may be produced. In any event, the catalyst does not become incorporated into the final product.

Suitable Friedel-Crafts catalysts include ferric chloride, zinc chloride, zinc bromide, ferric bromide, and ferric pivalate. Stronger Friedel-Crafts catalysts, such as aluminum chloride and stannic chloride, and other halides, such as cadmium chloride and tetra-n-butylammonium bromide, have been found not to be effective.

The molar ratio of the catalyst to the hyponitrite salt should be at least about 0.25:1, preferably at least about 0.5:1, and most preferably at least 1:1 or equimolar. When this molar ratio is less than about 0.25:1, the catalyst apparently combines with the hyponitrite salt rather than producing the desired reaction. Yields of the tertiary organic hyponitrite can be increased significantly by using a molar ratio greater than about 0.5:1 and the best yields usually can be obtained with a molar ratio of at least 1:1 or greater.

As mentioned above, the solvent is substantially neutral and is capable of dissolving the catalyst without inhibiting its catalytic activity. At present, monofunctional ethers or solvents which behave like a monofunctional ether are preferred. Solvents which tend to combine with the catalyst, such as 1,2-dimethoxyethane and other polyfunctional ethers, should be avoided because they tend to either inhibit or substantially eliminate the effectiveness of the catalyst.

Suitable solvents include ether, pentane, and other lower alkanes, tetrahydrofuran, isopropyl ether, di-n-butyl ether, methyl ethyl ether, tetrahydropyran, 2-methylfuran, and 1,10-dimethoxydecane.

The reaction can be carried out by first combining the tertiary organic halide, the solvent and the catalyst to form a solution or mixture. The resulting solution or mixture usually is cooled to room temperature prior to the addition of the hyponitrite salt because the reaction is highly exothermic. The hyponitrite salt is slowly added to the solution, preferably with some agitation or stirring to uniformly disperse the hyponitrite salt throughout the solution. The reaction is controlled by external cooling of the reaction mixture to maintain the temperature below the decomposition temperature of the tertiary organic hyponitrite being produced. The reaction mixture is usually maintained at a temperature of about $-10°$ to about 45° C., preferably below a temperature of about 30° C.

The reaction time will vary depending on the amount of and particular hyponitrite salt, organic halide, catalyst and solvent being used. Generally, the reaction time will be about 10 minutes to about 2 hours with reagent concentrations above 0.01 molar.

Upon completion of the reation, the solids (primarily the halide of the hyponitrite salt) can be separated from the reaction mixture in a suitable manner, such as by filtration or centrifugation. An organic layer in the resulting liquid portion contains the tertiary organic hyponitrite. This layer can be treated to remove the inorganic catalyst, such as by water extraction. The resulting solution may be used as such in the polymerization of ethylenically unsaturated compounds or the hyponitrite isolated therefrom, such as by evaporation of the solvent at a low temperature or by crystallization at a low temperature.

Without further elaboration, it is believed that one skilled in the art can, using the preceding description, utilize the invention to its fullest extent. The following examples are presented to exemplify preferred embodiments of the invention and should not be construed as limitations thereof.

EXAMPLE 1

0.6 g (0.005 mole) of zinc chloride, dried overnight at 130° C., was dissolved in 4 ml of ether and 4 ml of redistilled tert-butyl bromide. 0.53 g (0.005 mole) of a sodium hyponitrite was added to the solution at a temperature of 0° C. and while being stirred over period of several minutes. After stirring at 0° C. for an additional 35 minutes, the mixture was allowed to stand overnight at 5° C. and then filtered. The filtered white solid (water-soluble NaBr) was washed with ether. The combined filtrates were washed twice with 6 ml portions of ice water, dried with anhydrous sodium sulfate, and concentrated at 25° C. and 20 torr to a colorless crystalline mass. Crystallization of this mass from methanol at $-20°$ C. gave several crops of di-tert-butyl hyponitrite. The melting point for the first crop was found to be 80°–81.5° C. dec. The identity of the material was confirmed with IR and HMR spectral data.

EXAMPLE 2

0.4 g of sodium hyponitrite was slowly introduced into a solution containing 0.6 g anhydrous ferric chloride, 4 ml ether and 4 ml tert-butyl bromide over a 5 minute period with swirling and ocassional cooling below 45° C. with tap water. The reaction mixture was stirred for 75 minutes at room temperature and then allowed to stand overnight at 5° C. The mixture was processed in the manner described in Example 1 and 0.5 g (82%) of di-tert-butyl hyponitrite was recovered as an off-white solid. The HMR spectrum showed a singlet with only minor signals ascribed to impurities.

EXAMPLE 3

2.0 g of sodium hyponitrite was added to a solution containing 2.8 g ferric chloride, 15 ml tert-amyl chloride and 20 ml ether over a 10 minute period with swirling and ocassional cooling below 45° C. with tap water. After an additional 20 minutes, the mixture was filtered and the filtrate was washed with four portions of water, dried with magnesium sulfate and concentrated at 25° C. and 20 torr to produce 2.3 g (60%) of a rose-colored oil. Approximately 0.5 g of this material was chromatographed through silica gel (60–200 mesh) with pentane. The eluant was concentrated to give di-tert-amyl hyponitrite as a colorless oil. The identity of the material was confirmed with IR and HMR spectral data.

EXAMPLE 4

2.0 g of sodium hyponitrite was added in one portion to a solution containing 3.0 g zinc chloride, 14 ml tert-amyl bromide and 20 ml ether. An exothermic reaction occurred and the ether began to boil. The mixture was cooled in ice until the temperature dropped below 40° C. and then stirred magnetically at 25° C. for 30 minutes. The reaction mixture was then processed in the manner described in Example 3, except that sodium sulfate was used as a drying agent. The oil obtained on concentration at 20 torr was further concentrated below 1 torr for several minutes. The HMR spectrum of the resulting liquid (2.1 g) showed the presence of di-tert-amyl hyponitrite and minor singlets ascribed to the starting bromide. From integration of the HMR spectrum, the liquid was determined to be 80% pure which corresponds to an actual yield of 48%. The identify of the material was confirmed by IR spectral data.

EXAMPLE 5

0.5 g of tetra-n-butyl ammonium hyponitrite was added to a solution containing 0.15 g ferric chloride, 2 ml tert-butyl bromide and 2 ml ether. An additional 0.2 g of ferric chloride was added after a few minutes. The mixture was swirled for 10 minutes, allowed to stand for an additional 30 minutes and then filtered. The filtrate was diluted to 10 ml with isoctane and again filtered. Analysis of the solution by high pressure liquid chromatography indicated the presence of 21 mg (13%) of di-tert-butyl hyponitrite.

EXAMPLE 6

0.1 g of calcium hyponitrite was added to a solution containing 0.20 g chloride, 2 ml tert-butyl bromide and 2 ml ether. The mixture was swirled for several minutes and allowed to stand at 25° C. for 25 minutes. The mixture was extracted with 20 ml water and the organic phase was diluted to 10 ml with ether. Analysis of the solution by high pressure liquid chromatography indicated the presence of 6.3 mg (3.8%) of di-tert-butyl hyponitrite.

EXAMPLE 7

Small portions of ferric chloride were added to a mixture of 10 ml tert-amyl chloride and 25 ml ether and 2.0 g sodium hyponitrite. A sustained exothermic reaction did not occur until 0.8 g of the ferric chloride was added. This corresponds to a catalyst to hyponitrite salt molar ratio of approximately 0.26:1.

Another series of tests was run wherein varying amounts of ferric chloride was added to solutions containing 1 ml tert-butyl chloride, 1 ml ether and 0.1 g sodium hyponitrite to determine the effect of the catalyst concentration on the yield of organic hyponitrite. The liquid reaction product from each run was analyzed by high pressure liquid chromatagraphy to determine the amount of di-tert-butyl hyponitrite produced. The results of these tests are summarized in Table I.

TABLE I

Yield of Di-tert-Butyl Hyponitrite as Function of $FeCl_3$ Concentration

| Run No. | Molar Ratio of $FeCl_3$ to $Na_2N_2O_2$ | Yield, % |
|---|---|---|
| 1 | 0 (control) | <0.02 |
| 2 | 0.457:1 | 11 |
| 3 | 0.915:1 | 56 |
| 4 | 1.83:1 | 70 |

From these data, it can be seen that the catalyst to hyponitrite sale molar ratio should be at least 0.25:1 in order to obtain the desired product, that yields of the organic hyponitrite in excess of 11% can be obtained with a molar ratio of at least about 0.5:1, and that yields substantially in excess of 50% can be obtained with a molar ratio of 1:1 or more.

EXAMPLE 8

A series of tests was run wherein sodium hyponitrite was reacted with a tertiary organic halide in the presence of different metal salt catalysts, including ferric chloride and zinc bromide, in attempt to produce di-tert-butyl hyponitrite. Approximate equimolar amounts of the metal salt and sodium hyponitrite were used in each run. Tert-butyl bromide was used as the organic halide in all the tests, except Run 4 in which tert-butyl chloride was used. The results of these tests are summarized in Table II.

TABLE II

Yields of Di-tert-Butyl Hyponitrite With Different Metal Salts

| Run No. | Metal Salt | Solvent | Reaction Time, min. | Yields, % |
|---|---|---|---|---|
| 1 | $AlCl_3$ | ether | 40 | <8% (none isolated) |
| 2 | $SnCl_4$ | pentane | 30 | 9% |
| 3 | $CdCl_2$ | THF* | 60 | <2% |
| 4 | $FeCl_3$ | ether | 70 | 88% |
| 5 | $ZnBr_2$ | ether | 30 | 45% |

*Tetrahydrofuran

From these data it can be seen that stronger Friedel-Crafts catalysts, such a $AlCl_3$ and $SnCl_4$, and other metal salts, such as $CdCl_2$, were not effective for producing appreciable yeilds, even though an equimolar amount of catalyst and hyponitrite salt was used. On the other hand, $FeCl_3$ and $ZnBr_2$ produced yields of at least 45% or more with the same molar ratio.

From the foregoing description, one skilled in the art can easily ascertain the essential characteristics of the invention and, without departing from the spirit and scope thereof, make various changes and modifications to adapt it to various usages.

I claim:

1. A method for preparing a tertiary organic hyponitrite comprising reacting an alkali metal, alkaline earth, ammonium or substituted ammonium salt of hyponitrite with a tertiary organic halide having the general formula

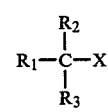

wherein $R_1$, $R_2$ and $R_3$ are aliphatic, substituted aliphatic or substituted aromatic groups and the bond between C and each $R_1$, $R_2$, and $R_3$ is connected to a saturated carbon and X is a halide, in the presence of a catalytic amount of a weak Friedel-Crafts catalyst which does not readily react with water and in a solution of substantially neutral solvent capable of dissolving said catalyst without substantially inhibiting its catalytic activity to produce the corresponding organic tertiary hyponitrite, while maintaining the reaction medium at a temperature below the decomposition temperature of said tertiary organic hyponitrite.

2. A method according to claim 1 wherein each $R_1$, $R_2$, and $R_3$ is the saturated aliphatic group.

3. A method according to claim 2 wherein X is bromide or chloride.

4. A method according to claim 1 wherein said hyponitrite salt is sodium hyponitrite.

5. A method according to claim 1 wherein said solvent is a monofunctional ether or a compound which behaves like a monofunctional ether.

6. A method according to claim 1 wherein the reaction medium is maintained at a temperature of about $-10°$ to about 45° C.

7. A method according to claim 1 wherein the molar ratio of said catalyst to said hyponitrite salt is at least about 0.25:1.

8. A method according to claim 7 wherein the molar ratio of said catalyst to said hyponitrite salt is at least 1:1.

9. A method according to claim 1 wherein said catalyst is ferric chloride, zinc chloride, zinc bromide or a mixture thereof.

10. A method for preparing a tertiary alkyl hyponitrite comprising reacting an alkali metal, an alkaline earth, ammonium or substituted ammonium salt of hyponitrite with a tertiary saturated alkyl halide in the presence of at least an equimolar amount, relative to said hyponitrite salt, of a weak Friedel-Crafts catalyst which does not readily react with water and in a solution of a substantially neutral solvent to produce the corresponding tertiary alkyl hyponitrite, while maintaining the reaction medium at a temperature below the decomposition of said tertiary alkyl hyponitrite.

11. A method according to claim 10 wherein said halide is bromide or chloride.

12. A method according to claim 11 wherein said hyponitrite salt is sodium hyponitrite.

13. A method according to claim 11 wherein said catalyst is ferric chloride, zinc chloride, zinc bromide or mixtures thereof.

14. A method according to claim 13 wherein said solvent is a monofunctional ether and the reaction medium is maintained at a temperature of about $-10°$ to about 45° C.

* * * * *